United States Patent
Matsubara

(10) Patent No.: US 12,235,196 B2
(45) Date of Patent: Feb. 25, 2025

(54) METHOD FOR PRETREATMENT OF BIOLOGICAL SAMPLE

(71) Applicant: SHIMADZU CORPORATION, Kyoto (JP)

(72) Inventor: Toshiya Matsubara, Columbia, MD (US)

(73) Assignee: SHIMADZU CORPORATION, Kyoto (JP)

( * ) Notice: Subject to any disclaimer, the term of this patent is extended or adjusted under 35 U.S.C. 154(b) by 800 days.

(21) Appl. No.: 17/264,887

(22) PCT Filed: Sep. 18, 2018

(86) PCT No.: PCT/JP2018/034434
§ 371 (c)(1),
(2) Date: Feb. 1, 2021

(87) PCT Pub. No.: WO2020/059013
PCT Pub. Date: Mar. 26, 2020

(65) Prior Publication Data
US 2021/0302286 A1    Sep. 30, 2021

(51) Int. Cl.
*G01N 1/38*    (2006.01)
*G01N 33/68*    (2006.01)

(52) U.S. Cl.
CPC ........... *G01N 1/38* (2013.01); *G01N 33/6848* (2013.01)

(58) Field of Classification Search
CPC ............................. G01N 1/38; G01N 33/6848
See application file for complete search history.

(56) References Cited

U.S. PATENT DOCUMENTS

2017/0059579 A1    3/2017 Toyama et al.

FOREIGN PATENT DOCUMENTS

JP    2017161447 A  *  9/2017
WO    2015/125216 A1    8/2015

OTHER PUBLICATIONS

International Search Report for PCT/JP2018/034434 dated Nov. 20, 2018 [PCT/ISA/210].
Written Opinion for PCT/JP2018/034434 dated Nov. 20, 2018 [PCT/ISA/237].

* cited by examiner

*Primary Examiner* — Jill A Warden
*Assistant Examiner* — Michael Stanley Gzybowski
(74) *Attorney, Agent, or Firm* — Sughrue Mion, PLLC

(57) ABSTRACT

The present invention provides a method for pretreatment of a biological sample in order to measure a protein contained in the biological sample by liquid chromatography/mass spectrometry. The method includes the step of adding an acetic acid aqueous solution to the biological sample, so as to prepare a pretreatment sample containing an acetic acid at a concentration ranging from 20 to 50 weight percent, both inclusive. In the present invention, a target protein contained in a biological sample is less prone to be adsorbed to a sample container, thereby resulting in an increased sensitivity of measuring the protein in the biological sample by mass spectrometry. Further, reproducibility of results of the mass spectrometry is improved, and reliability is increased.

2 Claims, 2 Drawing Sheets

METHOD FOR PRETREATMENT OF BIOLOGICAL SAMPLE

CROSS REFERENCE TO RELATED APPLICATIONS

This application is a National Stage of International Application No. PCT/JP2018/034434 filed Sep. 18, 2018.

TECHNICAL FIELD

The present invention relates to a method for pretreatment of a biological sample prior to measuring a protein contained in the biological sample by liquid chromatography/mass spectrometry.

BACKGROUND ART

It is known that an increase or a decrease in an amount of certain proteins contained in a biological sample such as blood or biotissue is associated with a specific disease, and such proteins are used as a biomarker for diagnosis or screening of the specific disease. Many of the proteins as the biomarker are contained only in trace amounts in the biological samples and, thus, the biomarker needs to be measured at high sensitivity and at high accuracy such that the diagnosis or screening based on the biomarker is accurate (see Patent Literature 1).

A liquid chromatography/mass spectrometry (LC/MS), which is a combination of a liquid chromatography and a mass spectrometry, serves as one of conventional methods for analysis of the protein or a peptide. Particularly, in recent years, as a technique for mass separation in a liquid chromatograph mass spectrometer has been developed, the LC/MS is capable of highly sensitive analysis and is becoming recognized as an essential method for quantitating the protein in trace amount.

Biological samples contain various components in addition to proteins, and some of the various components hinder an analysis target protein and are unwanted. Accordingly, before being subjected to the LC/MS, the biological sample is usually pretreated such that the unwanted components are removed. The pretreatment methods include one in which an antibody that is specifically bound to a target protein is used to isolate the target protein from the biological sample, and one in which a solid-phase extraction column is used to separate unwanted components from other components.

Before the pretreatment as described above, a biological sample that has been collected from a subject is put in a sample container and is diluted with an appropriate solvent or concentrated there, so that the biological sample is prepared in a state suitable for being pretreated. The biological sample thus prepared is then pretreated as described above. Further, the biological sample that has been pretreated is put in a sample container different from the one previously used, and is prepared at a concentration suitable for the liquid chromatography/mass spectrometry.

CITATION LIST

Patent Literature

Patent Literature 1: WO 2015/125216 A

SUMMARY OF INVENTION

Technical Problem

A sample is typically prepared in a sample container made of glass or a sample container made of plastic such as polypropylene (PP) or polyethylene (PE). However, when the biological sample is contained in a sample container of these types, some of the components in the biological sample are adsorbed to an inner surface of the sample container. More specifically, with the sample container of glass, ionic adsorption and hydrophobic adsorption occur due to silanol groups and siloxane, respectively, covering the surface of the sample container; and with the sample container of plastic, hydrophobic adsorption based on high-molecular polymer occurs. When target protein is contained only at trace amount and a part of the protein is adsorbed to the sample container and, further, the amount of the adsorbed protein varies, reproducibility of the LC/MS is degraded, resulting in a less reliable result of the LC/MS.

In view of this, as a conventional countermeasure, a surface treatment for preventing the adsorption is given to the sample container, or an adsorption inhibitor is added to the biological sample. The surface treatment of the sample container includes applying a coating agent, e.g., silicone, to the surface of the sample container or introducing hydrophilic groups into the surface of the sample container. However, the coating agent applied to the surface of the sample container may dissolve in the solvent used for preparing the biological sample, which may hinder ionization of the target protein (i.e., ion suppression) or detection of peak in the LC/MS. Further, the treatment of introducing the hydrophilic groups into the surface of the sample container is not sufficiently effective to prevent the hydrophobic adsorption.

Examples of the adsorption inhibitor added to the biological sample include an organic solvent (e.g., acetonitrile or methanol), a surfactant, and the peptide (BSA digest). However, the organic solvents may hinder retention of components in a reverse-phase separation column typically used in the LC/MS. When the retention of components in the reverse-phase separation column is hindered, a chromatogram shows an abnormal form of peak (e.g., peak split or peak tailing). Also, the surfactant causes ion source contamination or the ion suppression in the LC/MS, resulting in a decrease in sensitivity. Further, as the peptide added to the biological sample complicates composition of the biological sample, the ion suppression may cause a decrease in detection sensitivity.

As has been described above, any one of the conventional countermeasures against the adsorption of the protein to the sample container is not fully effective in the prevention or may hinder the analysis of the protein in the LC/MS.

Although, in the example described above, the biological sample is pretreated such that the unwanted components are removed, other ways to pretreat the biological sample (e.g., digesting or alkylating the protein) may have similar problems.

In view of the respects described above, an object of the present invention is to provide a method for pretreatment of the biological sample, in which the method is sufficiently effective to prevent the protein contained in the biological sample from being adsorbed to the sample container and not to hinder the measurement of the protein in the biological sample in the LC/MS.

Solution to Problem

To achieve the object above, the present invention provides a method for pretreatment of a biological sample in order to measure a protein contained in the biological sample by liquid chromatography/mass spectrometry.

The method includes the step of adding an acetic acid aqueous solution to the biological sample, so as to prepare a pretreatment sample containing an acetic acid at a concentration ranging from 20 to 50 weight percent, both inclusive.

To achieve the object above, the inventor of this application has studied and tested various methods to prevent the protein contained in the biological sample from being adsorbed to a sample container, and has found out that the protein is less prone to be adsorbed to the sample container when the biological sample contains the acetic acid at a relatively high concentration ranging from 20 to 50 weight percent. Further, when the pretreatment sample, which contains the acetic acid at such a high concentration and the biological sample, has been pretreated and when the pretreatment sample that has undergone the pretreatment is introduced into a liquid chromatograph mass spectrometer for analysis of the protein, the acetic acid at the high concentration does not hinder the analysis of the protein in the liquid chromatograph mass spectrometer.

The biological sample includes a sample (primary sample), such as blood (e.g., whole blood, plasma, or serum), interstitial fluid, saliva, or urine, collected from a subject and a sample secondarily obtained from the primary sample, such as tissue extract fluid, cell culture fluid, or cell extract fluid.

In the present invention, the subject is mostly a mammal, particularly a human.

The protein contained in the biological sample includes not only a protein contained in a body of the subject but also a protein included in a medicine administered into the body of the subject.

In the present invention, the biological sample collected from the subject is put in the sample container, the acetic acid aqueous solution is added therein, so that the pretreatment sample described above is prepared. Then, the pretreatment sample is subjected to appropriate pretreatment. In the present invention, the acetic acid aqueous solution is used to prepare the biological sample, and a main object of using the acetic acid aqueous solution is to dilute or concentrate the biological sample, adjust a pH value, or the like. Examples of the pretreatment includes: a treatment to separate an unwanted component from other components using a centrifugal separator, a solid-phase extraction column, a dialyzer, or the like; and a denaturation/reduction treatment, an alkylation treatment, or a protease treatment of the protein in the biological sample.

When the biological sample is put in the sample container, the protein in the biological sample immediately begins to be adsorbed to the sample container. Thus, preferably the acetic acid aqueous solution is added to the biological sample at a stage as early as possible. To this end, it is preferable that, for example, the acetic acid aqueous solution is added to the biological sample at the time when the biological sample collected from the subject is put in the sample container or, alternatively, the acetic acid aqueous solution is previously contained in an instrument to be used for collecting the biological sample from the subject.

For example, when the pretreatment sample is charged into the solid-phase extraction column to remove the unwanted component (as the pretreatment), the eluate flowing out of the solid-phase extraction column includes, besides the target component, an organic solvent for activating the filler of the solid-phase extraction column, a cleaning solution for washing unwanted component trapped in the filler, and an organic solvent for eluting the target protein. Thus, the concentration of acetic acid contained in the eluate falls below the range described above.

In view of this, the method described above preferably further includes the steps of:
doing a pretreatment using the pretreatment sample; and
adding acetic acid to the pretreatment sample that has undergone the pretreatment, so as to prepare an analysis sample which contains the acetic acid at the concentration ranging from 20 to 50 weight percent.

With the method above, between when the sample has been pretreated and when the sample is introduced into the LC/MS, the protein in the sample put in a sample container is less prone to be adsorbed to the sample container.

Advantageous Effects of Invention

In the present invention, a target protein contained in a biological sample is less prone to be adsorbed to a sample container, thereby resulting in an increased sensitivity of measuring the protein in the biological sample by mass spectrometry. Further, reproducibility of results of the mass spectrometry is improved, and reliability is increased.

DESCRIPTION OF EMBODIMENTS

The present invention provides a method for pretreatment of a biological sample in order to measure a protein contained in the biological sample by liquid chromatography/mass spectrometry. The method includes the step of adding an acetic acid aqueous solution to the biological sample, so as to prepare a pretreatment sample containing an acetic acid at a concentration within a predetermined range. The pretreatment sample preferably contains the acetic acid at a concentration ranging from 20 to 50 weight percent, more preferably at a concentration ranging from 35 to 45 weight percent.

With the method according to the present invention, the organic solvent, the surfactant, or the peptide, each added to the biological sample in a conventional method to prevent the protein or the peptide from being adsorbed to the sample container, is no longer required to be added or may be reduced in amount. Further, a surface treatment of the sample container, which has been required in the conventional method to prevent the protein or the peptide from being adsorbed to the sample container, is no longer required.

Figure 1:
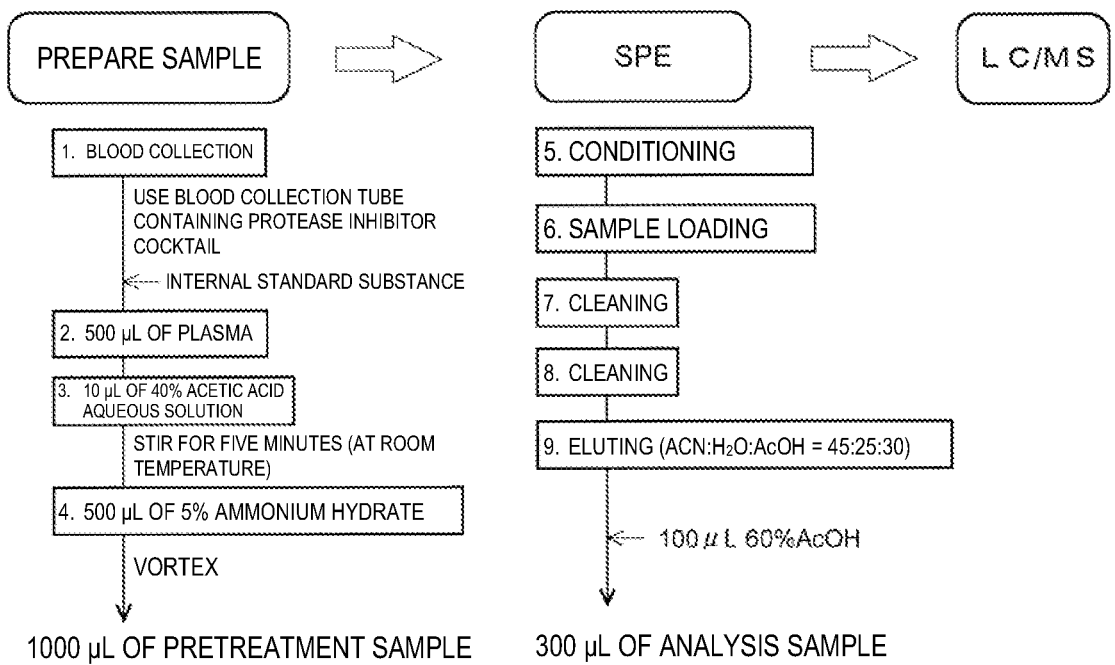
FIG. 1 is a diagram showing a schematic flow of a method for pretreatment of a sample according to the present invention.

FIG. 1 is a diagram showing a schematic flow of the method for pretreatment of the biological sample, the method according to the present invention. In an example described here, the biological sample corresponds to plasma, and the method for pretreatment of the plasma uses solid phase extraction.

<Sample Preparation>

Blood is collected from a subject. A blood collection tube is used to collect the blood from the subject, the blood collection tube where protease inhibitor cocktail is previously contained. After a stable isotope-labeled peptide or the like, as an internal standard substance, is added to the blood collected, the blood is separated into the plasma and a blood cell component by a centrifugal separator. 500 µL of the plasma is collected to be put in the sample container.

Next, 10 µL of a 40% acetic acid aqueous solution is added to the sample container to be stirred therein at room temperature for 5 to 10 minutes. As a result, each of an interaction between the proteins in the plasma and an interaction between the peptides in the plasma is released.

Subsequently, 500 µL of a 5% ammonium hydrate is added to the sample container and stirred by vortex mixer to obtain 1000 µL of the pretreatment sample.

<Solid Phase Extraction (SPE)>

Next, a solid-phase extraction column is used for pretreatment for removing an unwanted component contained in the pretreatment sample obtained above. The solid-phase extraction column may be a solid-phase extraction column using a non-polar filler of, for example, C18, or a solid-phase extraction column using an anion or cation exchange filler.

First, the filler of the solid-phase extraction column is wetted with an organic solvent (e.g., methanol) to activate the filler (conditioning).

Next, the pretreatment sample above (1000 µL) is flowed through the filler of the solid-phase extraction column at a predetermined flow rate (sample loading).

Subsequently, a cleaning solution is appropriately matched to polarity of the target protein and a polarity of the unwanted component, where both the protein and the unwanted component are contained in the pretreatment sample, and the cleaning solution is flowed through the filler (cleaning). As a result, the unwanted component that has been adsorbed into the filler is discharged from the solid-phase extraction column. The cleaning solution may be, for example, the 5% ammonium hydrate or a 10% acetonitrile (ACN).

Finally, an eluent is flowed through the filler to elute the protein as the target component that has been retained in the filler. The eluent may be, for example, a solution prepared by mixing the ACN, water, and the acetic acid in a ratio of 45/25/30. The acetic acid may be, for example, a 30% acetic acid.

A 60% acetic acid aqueous solution is added to an eluate obtained above, so as to prepare an analysis sample which contains the acetic acid at concentration of 40%. Then, the analysis sample is introduced into the liquid chromatograph mass spectrometer (LC/MS), so that the liquid chromatography/mass spectrometry (LC/MS/MS) is executed on the sample.

As has been described above, with the method for pretreatment of the sample, the method according to the present invention, the acetic acid aqueous solution is used as the solvent to prepare the pretreatment sample or the analysis sample. Apart from the acetic acid aqueous solution, the pretreatment may be carried out using the same solvents and instruments as in the conventional methods.

In the description above, the method for the pretreatment uses the solid phase extraction (SPE), but the method may also include the centrifugal separation performed in the step of preparing the sample. In other words, the method for pretreatment of the sample according to the present invention is applicable to a plurality of means of pretreatment, such that the protein contained in the biological sample is measured using the LC/MS or the LC/MS/MS.

In the description above, a biological sample collected from the subject is used as an example, but a peptide sample commercially available may also be the biological sample. In this case, the acetic acid aqueous solution may be used as a solvent for dissolving the peptide.

Example

Next, the present invention will be described specifically with reference to examples below, but the present invention is not limited to these examples. The following description assumes that "%" represents weight percent.

First Example

[Preparation of sample (pretreatment according to the present invention)] A glucagon sample commercially available (product name: "Glucagon Human"; manufacturer: Fujifilm Wako Pure Chemical Corporation) was put in a sample container made of polypropylene (product name: "Protein LoBind tubes"; manufacturer: Eppendorf Ltd), into which a sample preparation solvent was added. The sample preparation solvent was diluted by a diluent solvent step by step, so that five types of glucagon solution containing the glucagon at molar concentrations of 0.01 nM, 0.1 nM, 1 nM, 10 nM, and 100 nM or four types of glucagon solution containing the glucagon at molar concentrations of 0.01 nM, 0.1 nM, 1 nM, and 10 nM were prepared.

As the sample preparation solvent, any one of the 40% acetic acid aqueous solution, a 0.1% formic acid, a physiological salt solution, and a phosphate buffer solution was used; and as the diluent solvent, the 40% acetic acid aqueous solution or the 0.1% formic acid was used. Then, in each of seven different combinations of the sample preparation solvent and the diluent solvent, a set of the glucagon solutions containing the glucagon at the molar concentrations above was prepared.

[Liquid Chromatography/Mass Spectrometry (LC/MS/MS)]

Each of the seven sets of the glucagon solutions obtained above was introduced into the liquid chromatograph mass spectrometer (ultra-fast triple quadrupole LC/MS/MS system: LCMS-8060; Shimadzu Corporation), so that the LC/MS/MS was performed on the corresponding set of the glucagon solutions. The LC/MS/MS was performed three times on each of the seven sets.

Figure 2:
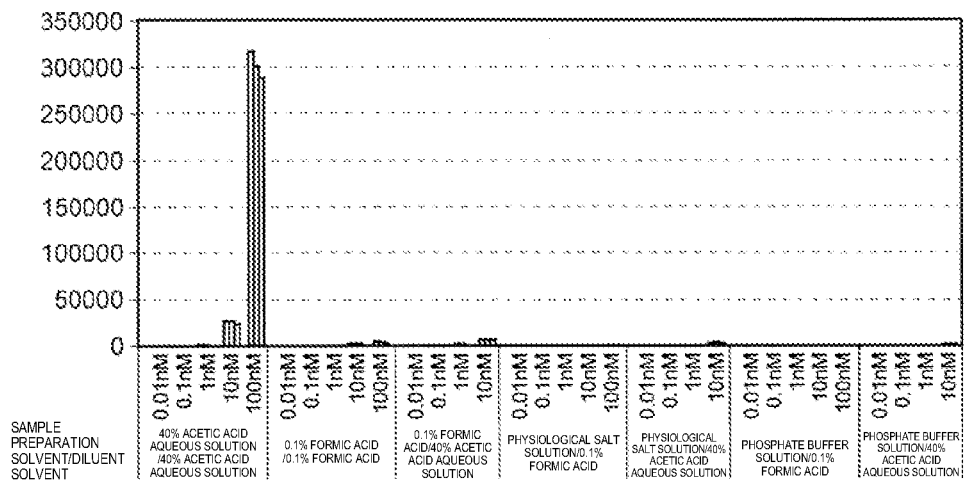
FIG. 2 shows a detection intensity (area value) in liquid chromatography/mass spectrometry (LC/MS/MS) performed after a peptide sample (glucagon) is prepared in various combinations of a sample preparation solvent and a diluent solvent.

As a result of the LC/MS/MS, a product spectrum of a precursor ion (m/z 940.10) derived from the glucagon was obtained, and based on the product spectrum, an intensity of a product ion (m/z 697.15) was acquired. FIG. 2 shows a result of each of the seven sets, each subjected to the LC/MS/MS three times. As seen from FIG. 2, when each of the sample preparation solvent and the diluent solvent corresponded to the 40% acetic acid aqueous solution, a detection intensity (area value) in the LC/MS/MS is significantly increased, as compared with the other combinations of the sample preparation solvent and the diluent solvent.

Second Example

With regard to an insulin sample commercially available (product name: "Human Insulin"; Sigma-Aldrich), as in the first example, the sample preparation solvent and the diluent solvent were used, so that five types of insulin solution containing the insulin at molar concentrations of 0.01 nM, 0.1 nM, 1 nM, 10 nM, and 100 nM or four types of insulin solution containing the insulin at molar concentrations of 0.01 nM, 0.1 nM, 1 nM, and 10 nM were prepared.

Figure 3:
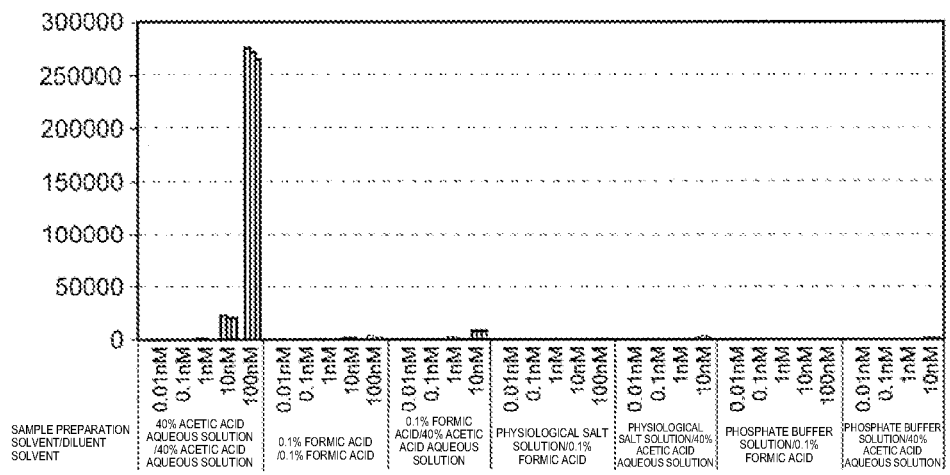
FIG. 3 shows a detection intensity (area value) in the LC/MS/MS performed after a peptide sample (insulin) is prepared in various combinations of the sample preparation solvent and the diluent solvent.

As a result, each of seven sets of the insulin solutions was obtained, and as in the first example, each of the seven sets was introduced into the liquid chromatograph mass spectrometer, so that the LC/MS/MS was performed on the corresponding set. As a result of the LC/MS/MS, a product spectrum of a precursor ion (m/z 1162.50) derived from the insulin was obtained, and based on the product spectrum, an intensity of a product ion (m/z [0]345.15) was acquired. FIG. 3 shows a result of each of the seven sets, each subjected to the LC/MS/MS three times. As seen from FIG. 3, in the second example too, when each of the sample preparation solvent and the diluent solvent corresponded to the 40% acetic acid aqueous solution, a detection intensity (area value) in the LC/MS/MS is significantly increased, as compared with the other combinations of the sample preparation solvent and the diluent solvent.

Third Example

As each of the sample preparation solvent and the diluent solvent, the acetic acid aqueous solution was prepared at concentration of 10%, 20%, 30%, 40%, and 50% (hereinafter, referred to as the 10% acetic acid aqueous solution, the 20% acetic acid aqueous solution, 30% acetic acid aqueous solution, the 40% acetic acid aqueous solution, and the 50% acetic acid aqueous solution). Then, in the same procedures as in the first example, the glucagon sample commercially available was prepared and diluted in a sample container made of polypropylene (PP) (product name: "TORAST-H Bio Vial"; Shimadzu GLC Ltd.), so that the glucagon solution containing the glucagon at molar concentration of 100 nM was obtained.

Additionally, as each of the sample preparation solvent and the diluent solvent, the 10% acetic acid aqueous solution, the 30% acetic acid aqueous solution, and the 50% acetic acid aqueous solution were prepared. Then, in the same procedures as in the first example, the glucagon sample commercially available was prepared and diluted in a sample container made of glass (product name: "1.5 mL Vial"; Shimadzu GLC Ltd.), so that the glucagon solution containing the glucagon at molar concentration of 100 nM was obtained.

Figure 4:
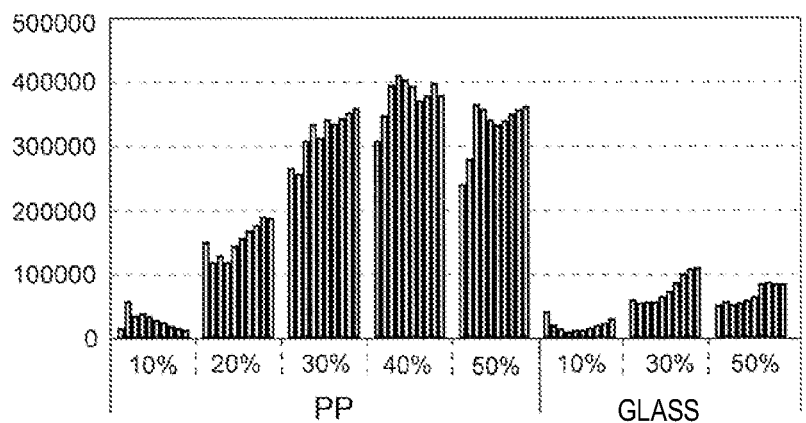
FIG. 4 shows a detection intensity (area value) in the LC/MS/MS performed after the peptide sample (glucagon) is prepared with the sample preparation solvent at various concentrations and the diluent solvent at various concentrations.

As in the first example, each of the glucagon solutions obtained above was introduced into the liquid chromatograph mass spectrometer where the LC/MS/MS was performed on the corresponding glucagon solution. As a result, an intensity of the product ion was acquired. Each of the glucagon solutions was subjected to the LC/MS/MS 10 times. FIG. 4 shows the results. As seen from FIG. 4, in any one of the sample container of PP and the sample container of glass, when each of the sample preparation solvent and the diluent solvent corresponded to the 10% acetic acid aqueous solution, the detection intensity was lowest. Additionally, when each of the sample preparation solvent and the diluent solvent corresponded to the 20% to 50% acetic acid aqueous solutions, the detection intensity was higher in the sample container of PP than in the sample container of glass; and particularly, when each of the sample preparation solvent and the diluent solvent corresponded to the 30% to 50% acetic acid aqueous solutions, the detection intensity was significantly higher in the sample container of PP.

As has been described above, when the sample container of PP was used, each of the 20% to 50% acetic acid aqueous solutions as the sample preparation solvent and the diluent solvent was highly effective to suppress an adsorption of the glucagon. Alternatively, when the sample container of glass was used, each of the 30% to 50% acetic acid aqueous solutions as the sample preparation solvent and the diluent solvent was also highly effective, although not as effective as with the sample container of PP, to suppress the adsorption of the glucagon.

Fourth Example

Figure 5:
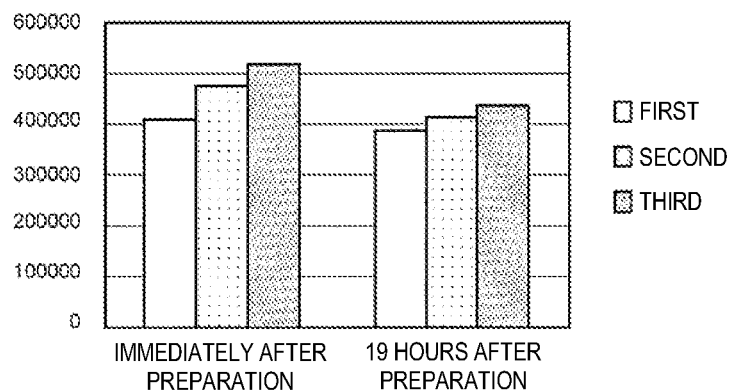
FIG. 5 shows a detection intensity (are value) in the LC/MS/MS performed after the peptide sample (glucagon) is prepared with an acetic acid aqueous solution containing an acetic acid at a concentration of 40%, the LC/MS/MS performed immediately after, and the LC/MS/MS performed 19 hours after.

Here, as each of the sample preparation solvent and the diluent solvent, the 40% acetic acid aqueous solution was prepared, and six of the glucagon solutions, each containing the glucagon at molar concentration of 100 nM, were prepared. Then, out of the six, three of the glucagon solutions were immediately introduced into the liquid chromatograph mass spectrometer where the LC/MS/MS was performed; and the other three were left at a temperature of 4° C. for 19 hours, before being introduced into the liquid chromatograph mass spectrometer where the LC/MS/MS was performed. FIG. 5 shows the results. Note that, each of the glucagon sample, the sample container, and the liquid chromatograph mass spectrometer used in this example was the same as in the first example.

As seen from FIG. 5, the results show no significant difference between the LC/MS/MS performed immediately after the preparation of the glucagon solutions and the LC/MS/MS performed 19 hours after the preparation. The results above presume that the glucagon solution, prepared by using the 40% acetic acid aqueous solution as the sample preparation solvent and the diluent solvent, was already effective to suppress the adsorption of the glucagon when prepared in the sample container.

The invention claimed is:

1. A method for pretreatment of a biological sample in order to measure a protein contained in the biological sample by liquid chromatography/mass spectrometry, the method comprising the steps of:
adding an acetic acid aqueous solution to the biological sample to prepare a pretreatment sample containing an acetic acid at a concentration ranging from 20 to 50 weight percent, both inclusive; and thereafter
adding acetic acid aqueous solution to the pretreatment sample, wherein the pretreatment sample has undergone a pretreatment, to prepare an analysis sample which contains acetic acid at a concentration ranging from 20 to 50 weight percent, both inclusive.

2. The method according to claim 1 wherein the analysis sample contains the acetic acid at a concentration ranging from 35 to 45 weight percent, both inclusive.

* * * * *